United States Patent [19]
Pinkerton et al.

[11] Patent Number: 6,003,321
[45] Date of Patent: Dec. 21, 1999

[54] OPEN FLOW HELIUM CRYOSTAT SYSTEM AND RELATED METHOD OF USING

[75] Inventors: A. Alan Pinkerton, Ottawa Hills, Ohio; Anthony Martin, Trenton, Mich.; Kristin Kirschbaum, Toledo, Ohio

[73] Assignee: The University of Toledo, Toledo, Ohio

[21] Appl. No.: 09/060,475

[22] Filed: Apr. 15, 1998

Related U.S. Application Data

[60] Provisional application No. 60/043,604, Apr. 15, 1997.

[51] Int. Cl.⁶ ............................................. F25B 19/00
[52] U.S. Cl. ............................. 62/51.1; 62/293; 62/320
[58] Field of Search ........................ 62/51.1, 51.2, 62/293, 320

[56] References Cited

U.S. PATENT DOCUMENTS

| | | | |
|---|---|---|---|
| 3,362,177 | 1/1968 | Case | 62/55 |
| 3,397,720 | 8/1968 | Jones | 138/149 |
| 3,433,028 | 3/1969 | Klee | 62/45 |
| 3,696,627 | 10/1972 | Longsworth | 62/51 |
| 4,107,946 | 8/1978 | Potter | 62/514 |
| 4,278,090 | 7/1981 | van Gerven | 62/522 |
| 4,296,610 | 10/1981 | Davis | 62/55 |
| 4,376,376 | 3/1983 | Gregory | 62/293 |
| 4,592,205 | 6/1986 | Brodbeck et al. | 13/2 |
| 4,646,525 | 3/1987 | Delacour et al. | 62/54 |
| 4,715,189 | 12/1987 | Hohenwarter | 62/64 |
| 4,739,633 | 4/1988 | Faris | 62/514 |
| 4,783,969 | 11/1988 | Hohol | 62/52 |
| 4,869,077 | 9/1989 | Grange et al. | 62/51.1 |
| 4,870,830 | 10/1989 | Hohenwarter et al. | 62/50.7 |
| 5,586,437 | 12/1996 | Blecher et al. | 62/47.1 |

*Primary Examiner*—Ronald Capossela
*Attorney, Agent, or Firm*—MacMillan, Sobanski & Todd, LLC

[57] ABSTRACT

An open flow helium cryostat system for cooling a sample crystal to be examined using X-ray diffraction, neutron diffraction, or a similar method. The cryostat system including a primary helium supply to provide a first stream of liquid helium onto the sample crystal and a secondary helium supply to provide a second stream of gaseous helium around at least a portion of the primary helium supply at a temperature warmer than the first stream of liquid helium to prevent the formation of ice on the sample crystal.

22 Claims, 5 Drawing Sheets

OPEN FLOW HELIUM CRYOSTAT SYSTEM AND RELATED METHOD OF USING

RELATED APPLICATION

This application claims the benefit of U.S. Provisional application Ser. No. 60/043,604, filed Apr. 15, 1997, incorporated by reference in its entirety.

FIELD OF THE INVENTION

The present invention relates to a device and method for state-of-the-art sample cooling; more specifically, a liquid helium, open flow, two stream cryostat for cooling a sample crystal to be examined using X-ray diffraction, neutron diffraction, or a similar method.

BACKGROUND

The advantages of using low temperatures for crystallography are well understood. Several commercially available systems such as the Oxford Cryostream use liquid nitrogen as a refrigerant and are relatively easy to use in conjunction with traditional methods of single crystal crystallography. However, a system which uses liquid helium as a refrigerant is much better than a nitrogen system because of the ability to achieve even lower temperatures which ultimately improves the quality of the crystallography (the minimum stable temperature achievable by a system using liquid nitrogen is about 85K; in contrast, a liquid helium system is capable achieving temperatures of 30K or lower). Unfortunately, the use of liquid helium as a refrigerant creates its own unique set of problems.

One problem with the use of helium as a refrigerant is the level of expertise required to operate a traditional system, as well as the cost to build it. For example, a typical system as used in the past involved mounting a closed cycle helium refrigerator on a large diffractometer, using, for example, a large Huber circle. The systems are complex in nature, thus requiring a high level of training for operators. Furthermore, a window made of beryllium is required which obscures the crystal and introduces systematic error into the data.

Another problem associated with the use of liquid helium as a refrigerant is the likelihood of frost or solid air forming on and around the inner nozzle of the cryostat or on the crystal itself or its support structure which inhibits accurate examining of the crystal. Frost/solid air formation is caused by the freezing of the gaseous components of air at the very low working temperatures used.

Based on the above, it is clear that a need exists for a cost effective liquid helium cooling system which allows examination of a sample crystal at a very low temperature without the problem of ice/solid air formation.

SUMMARY

The preferred embodiment of the present invention uses a commercially available cryostat which has been significantly modified, along with a variety of peripheral components, to solve the aforementioned problems. The device of the present invention includes a cryostat, a liquid helium source and back flow system, a stabilizing mechanism for the cryostat, and a sample retention device. The cryostat includes a cylindrical housing, a primary helium inlet, a secondary helium inlet, a safety valve, a vacuum port, an outer nozzle assembly, and an inner nozzle assembly.

In a preferred embodiment, the cryostat is a model LTR-3-110 Heli-tran® from ADP Cryogenics, Inc. It will be appreciated that the commercially available ADP cryostat must be modified in accordance with the present invention. First, one of the two factory installed thermocouples must be removed. The commercially available cryostat includes one factory installed thermocouple inside the cryostat housing near the primary helium inlet and one at the sample end of the inner nozzle assembly. To allow proper flow of the helium near the sample end, the thermocouple at that end is permanently removed. The second modification to the ADP cryostat includes shortening the quartz vacuum dewar so that the length of the dewar is compatible with the position of the nozzle. Finally, a heating element is added to the sample end of the vacuum dewar to prevent the formation of ice or solid air on the sample end of the quartz dewar or on the sample crystal itself There are six ports located around the periphery of the cylindrical housing of the cryostat. The primary helium inlet is a mechanical port which provides a first, "cold" stream of liquid helium with an entry point into the cryostat. The secondary helium inlet is also a mechanical port into the cryostat which allows a second, "warm" stream of helium to enter the cryostat. Lines internal to the cryostat allow both streams of helium to flow through to the sample end. One port provides access for instrumentation, another allows a safety valve to be connected to the cryostat, and yet another provides a pathway through which the cryostat may be evacuated. Finally, the cryostat includes an outer nozzle assembly/inner nozzle assembly combination which provides a path for the helium streams to reach the sample end of the device. The outer nozzle assembly includes an outer sleeve which houses the primary helium nozzle, a narrow tube connected to the primary helium inlet of the cryostat. The inner nozzle assembly includes a quartz dewar which is housed by an aluminum sleeve which in turn fits within the outer nozzle assembly. The inner nozzle assembly is sealed with respect to the outer nozzle assembly by a series of O-rings. The sample end of the quartz dewar is sheathed in a strip of lead foil which is then wrapped by a length of heating coil wire. In an alternate embodiment, the inner and outer nozzle assemblies may be constructed as one integral nozzle assembly, with the outer sleeve being made entirely of metal, thus eliminating the quartz dewar altogether. The heater wire may then be wrapped directly around the outer sleeve without the need for the lead foil.

The system also includes a liquid helium source and back flow system. The liquid helium source includes a standard liquid helium dewar connected to pressurized tanks of helium at one end and to the primary helium inlet of the cryostat at the other end. The primary helium inlet provides the cryostat with a supply of liquid ("cold") helium. The back flow system includes a valve and gauge arrangement connected to a flexible transfer line at one end and to the secondary helium inlet of the cryostat at the other end. The back flow system provides a "bleed off" stream of "warm" helium to the cryostat after performing its primary function of cooling the transfer line.

The cryostat stabilizing mechanism is a modification of the diffractometer used in the crystallography process. In the instant case, the clamping mechanism of a Siemens platform diffractometer was altered to accommodate the cryostat. The diffractometer includes a clamp mast attached at its base which provides support for the microscope of the diffractometer. An aluminum clamp was fashioned which attaches to the clamp mast above the clamp for the microscope and is clamped to the cryostat, providing a fixed, stable position over the sample crystal.

The sample retention mechanism used in the preferred embodiment of the present invention is a matter of standard practice; one part of a goniometer is used to examine the sample crystal. The goniometer head includes a brass pin which contains a glass fiber onto which the sample crystal is mounted.

The process related to the cryostat of the present invention is as follows. The cryostat and the outer/inner nozzle assembly is evacuated via the vacuum port. A first, "cold," stream of liquid helium is fed to the primary helium inlet of the cryostat. A second, "warm," stream of helium, which is obtained as a "bleed off" or back flow from the first stream is fed to the secondary helium inlet of the cryostat. Voltage to the heater wire is applied. The cold helium flows through the primary helium nozzle to the sample end of the quartz dewar. Initially, the cold helium is in a gaseous state but as the system cools the helium changes to a liquid. The warm helium flows through the outer and inner nozzle assemblies, surrounding the cold helium stream and isolating. The flow of both the cold and warm helium streams is balanced and the system is ready to conduct the examination of the sample crystal.

BRIEF DESCRIPTION OF THE DRAWINGS

Further features and other objects and advantages of this invention will become clear from the following detailed description made with reference to the drawings in which.

DETAILED DESCRIPTION

System Overview

The preferred embodiment of the present open flow helium cryostat system and related method is disclosed as shown in FIGS. 1–4 and is generally referred to by the reference numeral 100. The system 100 includes a cryostat 200, a helium source and back flow system 300, and a cryostat retention assembly 400. A sample retention assembly 500 and a diffractometer 600 (shown in part as a portion of the cryostat retention assembly 400) are not included in the present invention per se.

Cryostat

As shown in the figures, the cryostat 200 shown in FIGS. 1–4 is a modified off-the-shelf model LTR-3-110 Heli-tran® from ADP Cryogenics, Inc. The ADP cryostat was designed for use in experiments in the field of magnetic resonance, but was modified for use in the field of crystallography. Accordingly, any commercially available cryostat or custom-built cryostat could be used if constructed to the following configuration. The cryostat 200 is constructed of a cylindrical housing 201 made of non-magnetic stainless steel or equivalent. The cryostat 200 also includes six ports spaced at intervals around its periphery: a primary helium inlet 210, a secondary helium inlet 220, an instrumentation port 230, a safety valve port 240, a vacuum port 250, and an outer nozzle assembly 270, best shown in FIG. 2. The present invention also includes an inner nozzle assembly 260, which is slidably disposed within the outer nozzle assembly 270 and which will be described in greater detail further herein.

Figure 2:
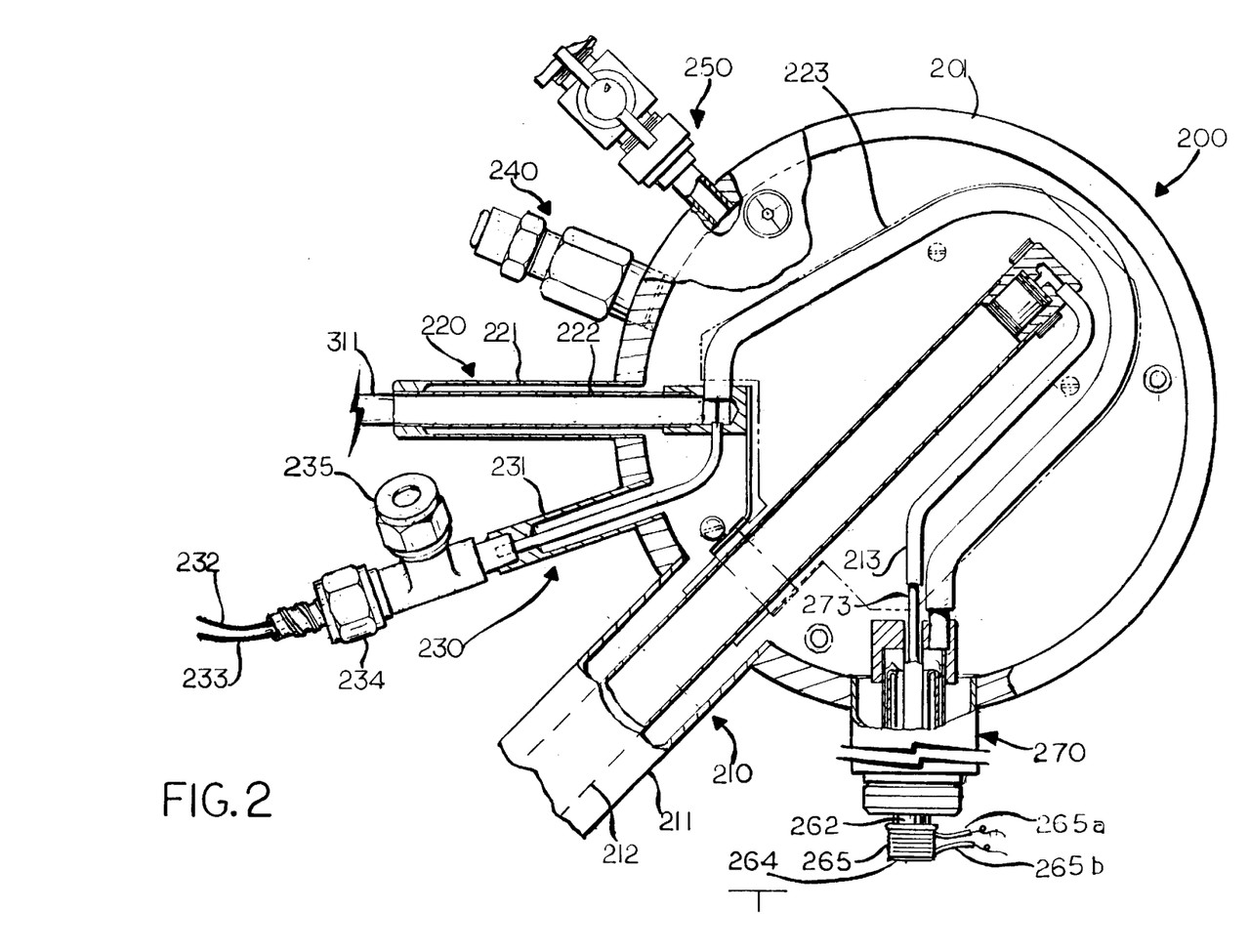
FIG. 2 shows a side elevational view of the cryostat of the invention shown in FIG. 1.

The primary helium inlet 210 is constructed of an outer sleeve 211 which surrounds an inner sleeve 212. The outer sleeve 211 is formed as an integral part of the cryostat housing 201 and is constructed of a like material. The end of the outer sleeve (not shown) is equipped with a fitting 214 of conventional construction which is capable of receiving a standard liquid helium transfer line. The inner sleeve 212 extends within the housing 201 of the cryostat and is connected to primary helium supply line 213, as shown in FIG. 2.

The secondary helium inlet 220 is similar to the primary helium inlet 210 in that it includes an outer sleeve 221 and an inner sleeve 222. The inner sleeve 222 also extends within the housing 201 of the cryostat 200 and is connected to a secondary helium supply line 223. The secondary helium inlet 220 is capable of receiving a back flow tube 311, to be discussed later herein. In an alternate embodiment, the secondary helium inlet 220 is relocated so that the back flow tube 311 bypasses the interior of the cryostat housing 201 and connects directly to the outer nozzle assembly 270.

The instrumentation port 230 includes an outer sleeve 231 equipped with a supplementary vacuum port 235 of conventional construction, and a standard fitting 234 for adequately sealing the instrumentation port 230 which receives thermocouple wires 232 and 233.

The safety valve port 240 is also formed as an integral part of the ADP cryostat housing 201 and is equipped with a factory-installed safety valve 241.

The vacuum port 250 is outfitted with factory-installed fitting 251 which is capable of being connected with a standard vacuum pump (not shown).

Figure 1:
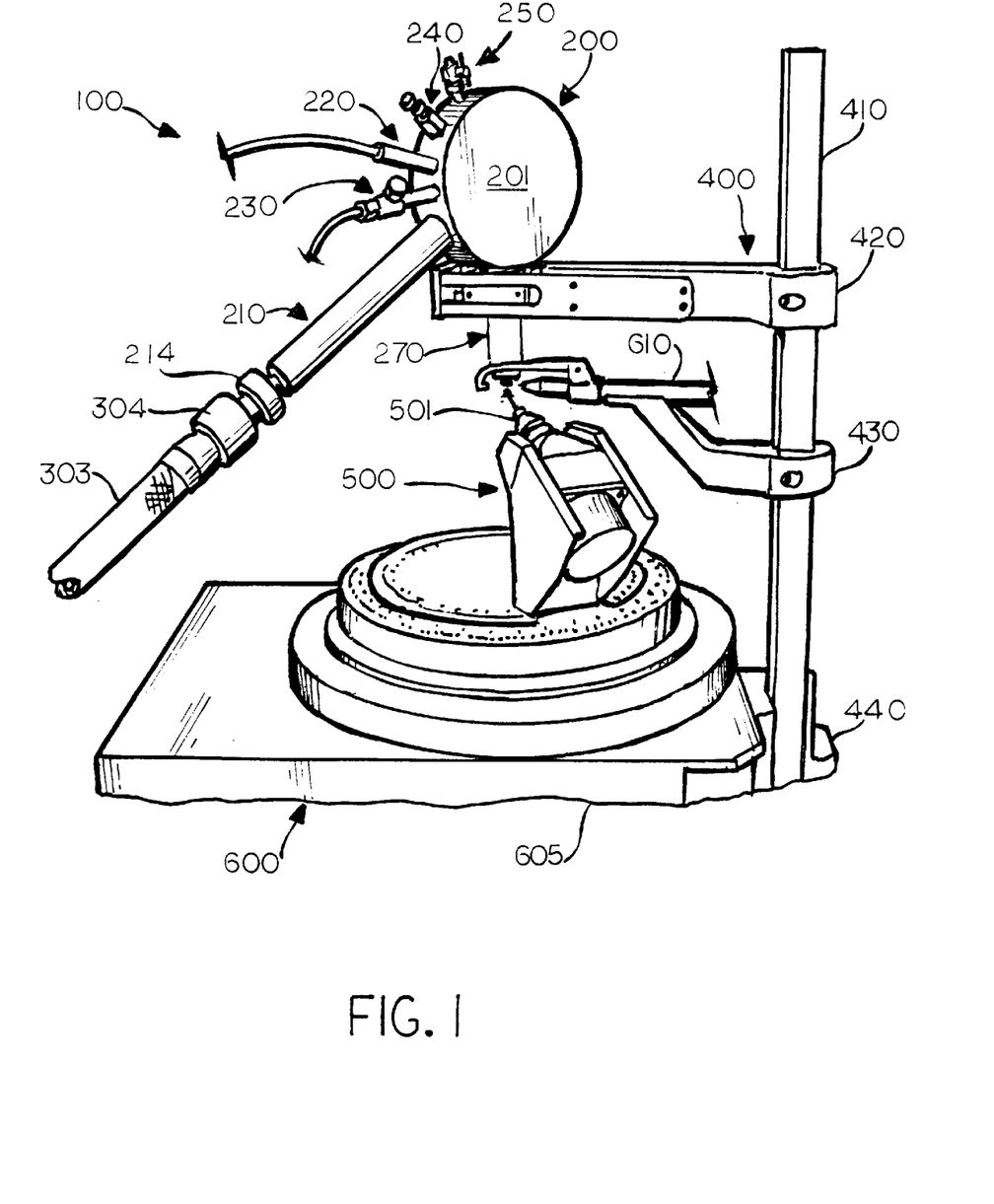
FIG. 1 shows a perspective view of the preferred embodiment of the present invention, except for the helium source and back flow system.
Figures 1A, 3A:
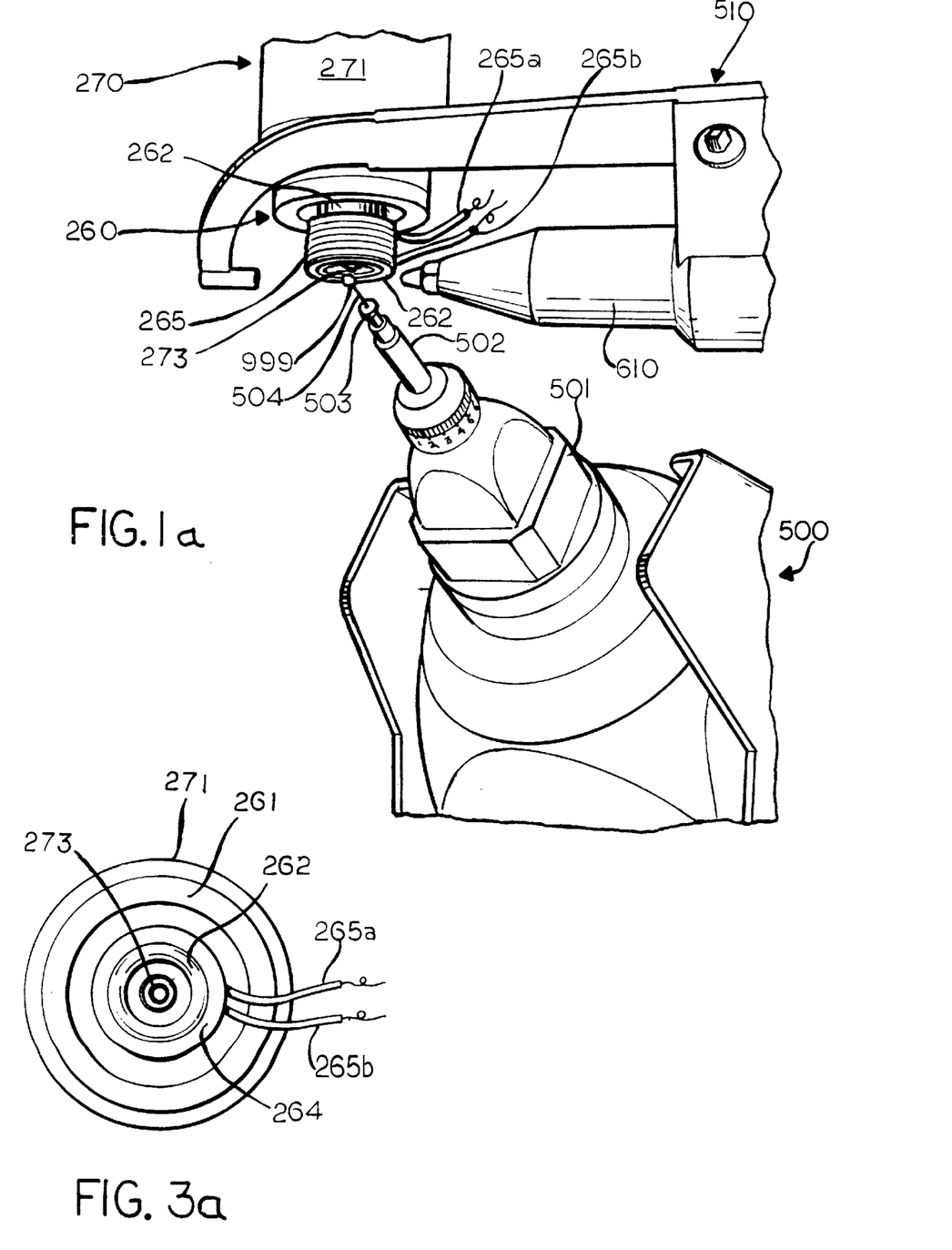
FIG. 1a shows an enlarged perspective view of the sample retention mechanism and the lower portion of the outer and inner nozzle assemblies of the invention shown in FIG. 1.
FIG. 3a shows a sectional view along line 3a—3a of the outer and inner nozzle assemblies shown in FIG. 3.
Figure 3:
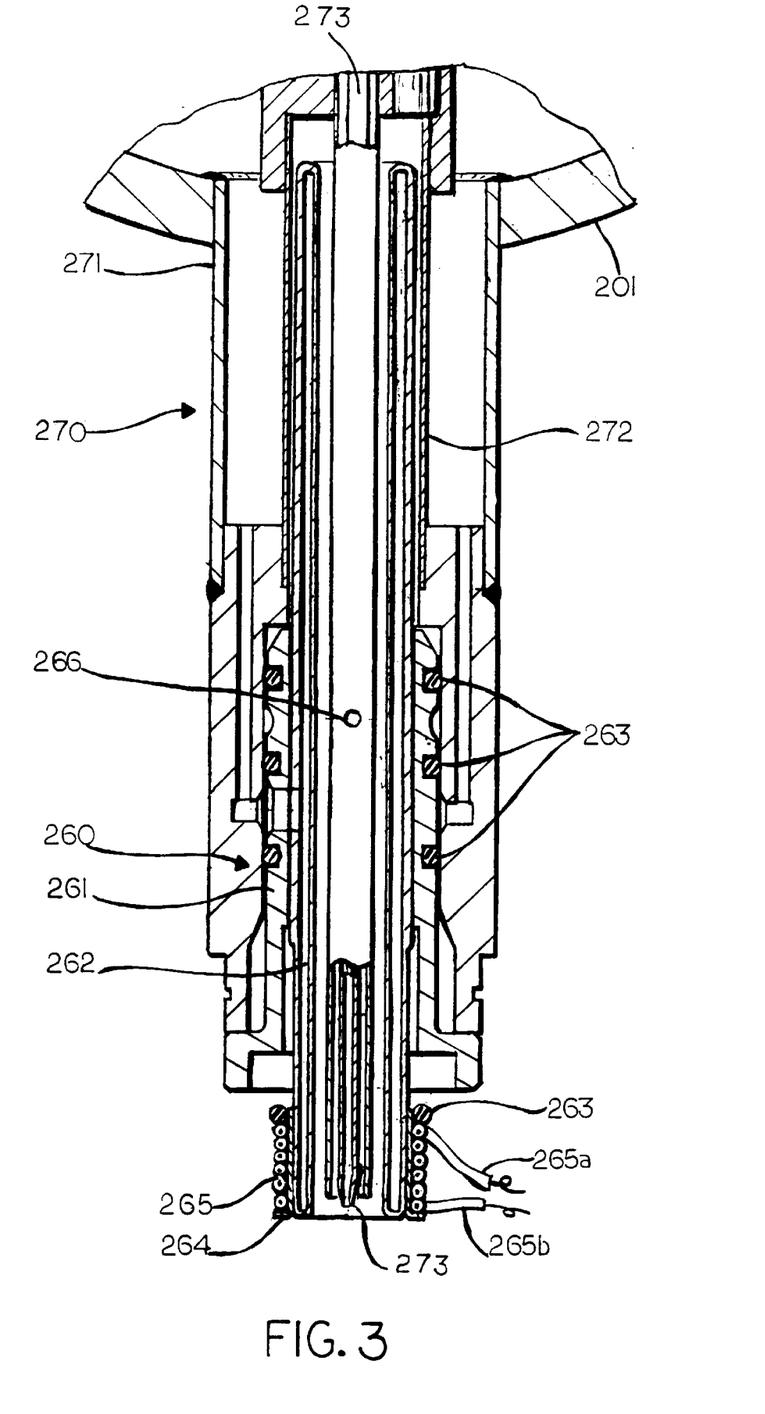
FIG. 3 shows a side elevational view of the outer and inner nozzle assemblies of the invention shown in FIG. 1.

The outer nozzle assembly 270, best shown in FIGS. 3 and 3a, includes an outer sleeve 271, an inner sleeve 272, and a primary helium nozzle 273. The outer sleeve 271 is formed as an integral part of the cryostat housing 201. The inner sleeve 272 is disposed within the outer sleeve 271 as shown. The primary helium nozzle 273 is located in the center of the inner sleeve 272 and extends from the primary helium supply line 213 (in the interior of the cryostat housing 201).

The inner nozzle assembly 260 includes an outer sleeve 261, a quartz dewar 262, a variety of O-rings 263, lead foil 264, heater wire 265, heater wire leads 265a and 265b, and an alignment hole 266. The outer sleeve 261 of the inner nozzle assembly 260 is made such the outer diameter of the outer sleeve 261 is slightly less that the inner diameter of the inner sleeve 272 of the outer nozzle assembly 270; in other words, the inner nozzle assembly 260 slides within the outer nozzle assembly 270 as shown in FIG. 3. The inner nozzle assembly 260 is sealed with respect to the outer nozzle assembly 270 by a series of O-rings 263. The sample end of the quartz dewar 262 is sheathed in lead foil 264 and then wrapped with heater wire 265. The heater wire leads 265a and 265b are connected to a voltage source (not shown). When the inner nozzle assembly 260 is correctly positioned within the outer nozzle assembly 270, the primary helium nozzle 273 is in close physical proximity with the sample end of the quartz dewar 262.

Helium Source

Figure 4:
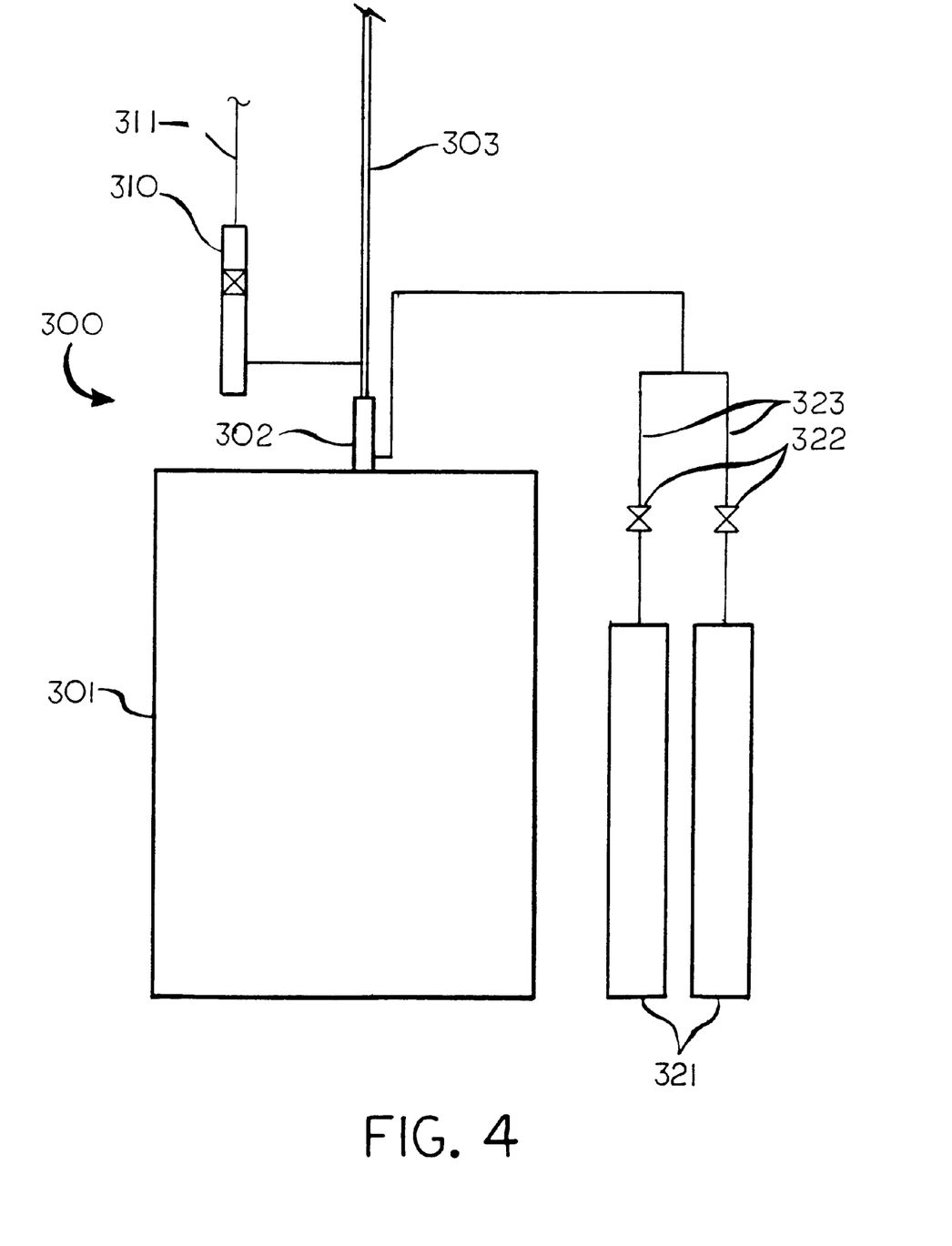
FIG. 4 shows a block diagram of the helium source and recirculation system of the invention shown in FIG. 1.

The helium source and back flow system 300 includes a conventional dewar 301 for containing liquid helium, a dewar adapter 302, a valve and gauge arrangement 310, at least one tank 321 of pressurized helium and related isolation valves 323, along with a variety of lines 303, 311, and 322 to connect the components. A block diagram of the helium source and back flow system 300 is shown in FIG. 4. Technical details of the helium source and back flow system 300 are disclosed in U.S. Pat. Nos. 3,696,627 and 3,706,209, along with ADP's "Model LTR-3 Liquid Transfer Heli-Tran Refrigerator Technical Manual," all of which are herein incorporated by reference.

The helium dewar 301 is of conventional construction, i.e., a double-walled glass vessel, evacuated between the walls, with a stainless steel housing (not shown) and fitted with a standard outlet fitting (not shown). The dewar adapter 302 includes a valve and gauge arrangement 310 as disclosed in the aforementioned Technical Manual. A flexible, liquid cryogen transfer line 303 is connected to the dewar adapter 302 at one end and to the primary helium inlet 210 of the cryostat 200 via fitting 304 at the other end. Also connected to the dewar adapter 302 is the valve and gauge arrangement 310 which is described in the Technical Manual. The valve and gauge arrangement 310 provides a "bleed-off" of "warn" helium to the cryostat 200 at an approximate pressure of 25–30 psi, the function of which is discussed in detail later herein. The back flow line 311 which is constructed of plastic tubing or the like is connected to the valve and gauge arrangement 310 at one end and to the secondary helium inlet 220 of the cryostat 200. The pressurized helium cylinders 321 (which are at an approximate pressure of 8–10 psi) are connected to the dewar adapter 302 via pressurized helium supply lines 322 and 324. Isolation valves 323, as shown in FIG. 4, are of standard construction and allow the helium tanks 321 to be replaced without interrupting the operation of the system 300.

Cryostat retention

The cryostat retention assembly 400, best shown in FIG. 1, is a clamping mechanism which is a modification of the existing clamping system (not shown) of the Siemens platform diffractometer 600. The cryostat retention assembly 400 includes clamp mast 410, cryostat clamp 420, and clamp base 440. The original clamp mast (not shown) is used to support a microscope 610 of the diffractometer 600. The clamp base 440 is attached to the diffractometer platform 605. The lengthened clamp mast 410 is attached to the clamp base 440. A cryostat clamp 420 is attached to the clamp mast 410 at one end and to the outer nozzle assembly 270 of the cryostat 200 at the other end. The cryostat clamp 420 is fashioned from aluminum or like material and includes position adjustment screws (not shown). Of course, the cryostat retention system 400 must be sturdy enough to support the weight of the cryostat 200, the helium transfer line 303, and all associated hardware.

Sample Retention

The sample retention assembly 500, best shown in FIG. 1A, is constructed of a portion of a goniometer (not shown) which is typically used to measure and record the positional data of the sample crystal 999. The sample retention assembly 500 includes a goniometer head 501, a sample rod 502, a receptacle pin 503, and a fiber 504. The sample rod 502 is attached to the goniometer head 501. The receptacle pin 503 is attached to the end of the sample rod 502 and the fiber 504 is fixed to the end of the receptacle pin 503, usually with epoxy resin or the like.

Operation

The operation of the present invention is as follows. The cryostat 200 is put in place by attaching cryostat clamp 420 onto the clamping mast 410 and then onto the outer sleeve 271 of the outer nozzle assembly 270. A sample crystal 999 is mounted on the fiber 504 of the sample retention assembly 500. The locations of the sample crystal 999 and sample end of the quartz dewar 262 are adjusted such that the dewar 262 is directly above the sample crystal 999 which is accurately centered in the X-ray beam. A primary (cold) and secondary (warm) helium flow are initiated by activating the helium source and back flow system 300. The stream of cold helium flows from the liquid helium dewar 301 through the dewar adapter 302, through the liquid helium transfer line 303, into the primary helium inlet 210 of the cryostat 200, through the primary helium supply line 213, into and through the primary helium nozzle 273, onto the sample crystal 999 and into the atmosphere. The flow of the cold helium stream starts in a gaseous state but is converted to a liquid state as the temperature of the system approaches about 4K, causing the temperature of the sample crystal 999 to fall to less than 30K. At the same time, a stream of warm helium flows from the valve and gauge arrangement 310, through the back flow tube 311, into the secondary helium inlet 220 of the cryostat 200, through the secondary helium supply line 223, into the passage of the outer nozzle assembly 270 between the outer sleeve 271 and inner sleeve 272, past the sample end of the quartz dewar 262 and into the atmosphere. The heat transfer between the ambient air and the plastic back flow tube 311 gives the warm helium its "heated" quality. Because of the temperature involved, the warm helium remains in a gaseous state throughout its flow path.

The heating process which takes place at the sample end of the quartz dewar 262 of the inner nozzle assembly 260 is critical for preventing the formation of ice/solid air on the dewar 262, the fiber 504, or the sample crystal 999 itself.

The heater wire leads 265a and 265b are connected to an external voltage source (not shown). As voltage is applied, the heater wire 265, along with the lead foil 264, are heated, thus preventing the formation of ice/solid air on any of the problem areas mentioned.

The patent and documents described above are hereby incorporated by reference in their entirety.

Having described presently preferred embodiments of the invention the invention may be otherwise embodied within scope of the appended claims.

What is claimed is:

1. An open flow helium cryostat system for cooling a sample crystal, the cryostat system comprising:
    a primary helium supply to provide a first stream of helium onto the sample crystal; and
    a secondary helium supply to provide a second stream of helium around at least a portion of the primary helium supply at a temperature warmer than the first stream of helium to prevent the formation of ice solid air on the sample crystal.

2. An open flow helium cryostat system for cooling a sample crystal to be examined, the cryostat system comprising:
    a housing having a primary helium inlet and a secondary helium inlet,
        the primary helium inlet including an outer sleeve surrounding an inner sleeve, the outer sleeve formed as an integral part of the housing and receives the inner sleeve in communication with a primary helium supply line;

the secondary helium inlet including an outer sleeve surrounding an inner sleeve, the outer sleeve formed as an integral part of the housing and receives the inner sleeve in communication with a secondary helium supply line;

an outer nozzle assembly including an outer sleeve, an inner sleeve and a primary helium nozzle, the outer sleeve formed integral with the housing and receiving an inner sleeve accommodating therein a primary helium nozzle defining a passage there between, the primary helium nozzle in communication with the primary helium supply line and the passage in communication with the secondary helium supply line.

3. An open flow helium cryostat system for cooling a sample crystal, comprising:

a housing;

a primary helium inlet connected to said housing for providing a primary source of helium at a first temperature onto the sample crystal;

a secondary helium inlet connected to said housing for providing a secondary source of helium at a second temperature; and an outer nozzle assembly connected to said housing for providing the primary source of helium and the secondary source of helium, wherein the second temperature of the secondary source of helium is at a higher temperature than the first temperature of the primary source of helium, thereby preventing the formation of a frozen substance on the sample crystal.

4. The cryostat system according to claim 3, wherein said outer nozzle includes an outer sleeve formed integrally with said housing, an inner sleeve disposed within said outer sleeve, and a primary helium nozzle disposed within said inner sleeve and in fluid communication with the primary source of helium.

5. The cryostat system according to claim 4, further comprising an inner nozzle assembly including an outer sleeve and a quartz dewar disposed within said outer sleeve, wherein an outer diameter of said outer sleeve of said inner nozzle is less than an inner diameter of said inner sleeve of said outer nozzle for slidably disposing said inner nozzle assembly within said outer nozzle assembly.

6. The cryostat system according to claim 5, further comprising heating means for heating an end of said quartz dewar proximate to the sample crystal.

7. The cryostat system according to claim 6, wherein said heating means comprises a foil wrapped around said proximate end of said quartz dewar and a heater wire wrapped around said foil, wherein a temperature of said foil and said heater wire is raised when electrical energy is applied to said heater wire, thereby preventing the formation of a frozen substance on the sample crystal.

8. The crystal system according to claim 3, wherein said primary helium inlet comprises an outer sleeve integral with said housing, and an inner sleeve disposed within said outer sleeve, one end of said inner sleeve extending within said housing and the other end of said inner sleeve connected to a primary helium supply line.

9. The crystal system according to claim 3, wherein said secondary helium inlet comprises an outer sleeve integral with said housing, and an inner sleeve disposed within said outer sleeve, one end of said inner sleeve extending within said housing, and the other end of said inner sleeve connected to a secondary helium supply line.

10. The crystal system according to claim 9, further comprising a back flow tube disposed within said inner sleeve, one end of said back flow tube connected to a valve and gauge arrangement, and the other end of said back flow tube connected to said secondary helium inlet, wherein a temperature of the secondary source of helium is raised when passing through said back flow tube, thereby preventing the formation of a frozen substance on the sample crystal.

11. The cryostat system according to claim 3, further including a cryostat retention assembly for supporting said housing.

12. An open flow helium cryostat system for cooling a sample crystal, comprising:

a cryostat;

a helium source and back flow system connected to said cryostat the helium source providing a first stream of helium and the back flow system providing a second stream of helium which is a bleed off or back flow from the first stream; and a cryostat retention assembly for supporting said cryostat.

13. The cryostat system according to claim 12, further comprising an outer nozzle assembly connected to said cryostat, and an inner nozzle assembly disposed within said outer nozzle assembly.

14. The cryostat system according to claim 13, wherein said inner nozzle assembly includes an outer sleeve and a quartz dewar disposed within said outer sleeve, wherein an outer diameter of said outer sleeve of said inner nozzle is less than an inner diameter of said inner sleeve of said outer nozzle for slidably disposing said inner nozzle assembly within said outer nozzle assembly.

15. The cryostat system according to claim 14, further comprising means for heating an end of said quartz dewar proximate to the sample crystal, thereby preventing the formation of frozen substances on the sample crystal.

16. The cryostat system according to claim 12, wherein said cryostat comprises a housing, said housing including a primary helium inlet port receiving said first stream of helium and a secondary helium inlet port receiving said second stream of helium.

17. The cryostat system according to claim 16, wherein said primary helium inlet port comprises an outer sleeve integral with said housing and an inner sleeve disposed within said outer sleeve, one end of said inner sleeve extending into said housing of said cryostat and the other end of said inner sleeve connected to said helium source.

18. The cryostat system according to claim 16, wherein said secondary helium inlet port comprises an outer sleeve integral with said housing, and an inner sleeve disposed within said outer sleeve, one end of said inner sleeve extending within said housing, and the other end of said inner sleeve connected to said back flow system.

19. The cryostat system according to claim 18, further comprising a back flow tube disposed within said inner sleeve, one end of said back flow tube connected to a valve and gauge arrangement of said back flow system, and the other end of said back flow tube connected to said secondary helium inlet, wherein a temperature of the second stream of helium is raised when passing through said back flow tube, thereby preventing the formation of a frozen substance on the sample crystal.

20. A method for cooling a sample crystal, the method comprising the steps of:

mounting the sample crystal on a sample retention assembly;

causing helium from a primary source of helium to flow onto the sample crystal at a first temperature; and causing helium from a secondary source of helium to flow around at least a portion of the primary helium supply at a second temperature, whereby the second temperature of the secondary source of helium is at a higher temperature than the first temperature of the primary source of helium, thereby preventing the formation of a frozen substance on the sample crystal.

21. The method according to claim 20, further comprising the step of passing the secondary source of helium through a back flow tube to increase the second temperature of the secondary source of helium.

22. The method according to claim 20, further comprising the step of heating the secondary source of helium at an outer nozzle assembly to increase the second temperature of the secondary source of helium.

* * * * *